United States Patent [19]

Tanabe et al.

[11] Patent Number: 4,842,590
[45] Date of Patent: Jun. 27, 1989

[54] CATHETER AND METHOD FOR MAKING

[75] Inventors: Susumu Tanabe, Fujinomiya; Tatsuo Suzuki, Machida, all of Japan

[73] Assignee: Terumo Kabushiki Kaisha, Tokyo, Japan

[21] Appl. No.: 204,965

[22] Filed: Jun. 2, 1988

Related U.S. Application Data

[63] Continuation of Ser. No. 918,613, Oct. 10, 1986, abandoned, which is a continuation of Ser. No. 655,333, Sep. 27, 1984, abandoned.

[30] Foreign Application Priority Data

Dec. 14, 1983 [JP] Japan .................. 58-234292

[51] Int. Cl.$^4$ ............................. A61M 25/00
[52] U.S. Cl. ................... 604/282; 128/656; 128/658
[58] Field of Search ............ 604/95, 280, 282; 128/656, 658

[56] References Cited

U.S. PATENT DOCUMENTS

| | | | |
|---|---|---|---|
| 3,470,869 | 10/1969 | Fenton et al. | 128/658 |
| 3,485,234 | 12/1969 | Stevens. | |
| 3,965,909 | 6/1976 | Waddell et al. | |
| 4,385,635 | 5/1983 | Ruiz | 604/280 X |
| 4,425,919 | 1/1984 | Alston, Jr. et al. | 604/282 X |
| 4,498,473 | 2/1985 | Gerey | 604/282 X |

FOREIGN PATENT DOCUMENTS

| | | | |
|---|---|---|---|
| 0033659 | 8/1981 | European Pat. Off. | 128/658 |
| 2043201 | 10/1980 | United Kingdom. | |

Primary Examiner—Ferris H. Lander
Attorney, Agent, or Firm—Frishauf, Holtz, Goodman & Woodward

[57] ABSTRACT

In a catheter comprising a proximal inner tube having a reinforcing layer applied thereto and a distal inner tube made of a material having different physical properties from those of the proximal inner tube, the proximal and distal inner tubes are axially integrally connected such that the outer surface of the proximal inner tube is substantially smooth and continuous to that of the distal inner tube, and a sheath continuously covers the proximal and distal inner tubes. The catheter is produced by axially integrally joining proximal and distal inner tubes and continuously covering the interconnected tubes with a sheath.

33 Claims, 4 Drawing Sheets

CATHETER AND METHOD FOR MAKING

This application is a continuation of application Ser. No. 918,613, filed Oct. 10, 1986 which in turn is a continuation of Ser. No. 655,333 filed on Sept. 27, 1984 both now abandoned.

BACKGROUND OF THE INVENTION

This invention relates to a catheter and a method for making the same.

When a catheter is inserted into a blood vessel or other body cavity, it is guided in with a guide or deflector wire. The catheter can be advanced to a destined location for medical treatment or diagnosis while controlling the direction of the catheter tip.

The body portion of such a catheter must have a certain degree of rigidity or relatively low flexibility while the tip portion must have a certain degree of softness or a relatively high flexibility and sometimes be plastically deformable to permit bending to a desired shape. In particular, intravascular catheters which are inserted and advanced into blood vessels must have a tip portion with a relatively high flexibility to prevent the catheter from damaging the inner wall of the vessel. At the same time, the body portion must have a relatively low flexibility to allow the force used to advance the catheter to be properly transmitted to the tip portion. In some cases, the tip portion of the catheter must be plastically deformable to permit bending to ensure proper insertion of the catheter in different cavities and areas of the body, which often differ considerably in shape from patient to patient.

SUMMARY OF THE INVENTION

An object of the present invention is to provide a catheter in which a body portion and a tip portion made of materials having different physical properties are integrally connected without forming a step at the joint therebetween.

Another object of the present invention is to provide a method for producing a catheter by integrally connecting body and tip portions of materials having different physical properties without forming a step at the joint therebetween.

According to the present invention, there is provided a catheter comprising a body portion including a proximal inner tube and a reinforcing layer embedded therein, a tip portion including a distal inner tube axially interconnected to the body portion, the distal inner tube being made of a material having different physical properties from those of the proximal inner tube, a sheath continuously covering the body portion and the distal inner tube, wherein the outer surface of the body portion is substantially smooth and continuous to that of the distal inner tube.

In one preferred embodiment of the present invention, the distal inner tube is made of a more flexible material than the proximal inner tube. For instance, the proximal inner tube is made of a polyamide elastomer and the distal inner tube is made of a plasticized polyamide elastomer.

In another preferred embodiment, the distal inner tube is made of a more plastically deformable material than the proximal inner tube. For instance, the proximal inner tube is made of a polyamaide elastomer and the distal inner tube is made of a polyethylene.

Preferably, the reinforcing layer is braided. The reinforcing layer is most preferably embedded in to the outer surface of the proximal inner tube. The reinforcing layer should preferably have an outer diameter substantially equal to that of the distal inner tube.

The material of which the distal inner tube is made may contain a radiopaque substance while the material of which the sheath is made is free of a radiopaque substance.

According to another aspect of the present invention, there is provided a method for producing a catheter comprising the steps of molding a proximal inner tube, applying a reinforcing layer onto the proximal inner tube, molding a distal inner tube from a material having different physical properties from those of the proximal inner tube, axially interconnecting the proximal inner tube to the distal inner tube with the outer surface of the proximal inner tube being substantially smooth and continuous to that of the distal inner tube, and continuously covering the interconnected proximal and distal inner tubes with a smooth continuous sheath.

The reinforcing layer may be applied to the proximal inner tube by placing reinforcing filaments or wires about the proximal inner tube and passing the proximal inner tube and wire braid through a heated die to thereby embed the wire braid in the outer surface of the proximal inner tube.

Alternatively, the reinforcing layer may be applied to the proximal inner tube by placing reinforcing filaments or wires about the proximal inner tube and successively passing the proximal inner tube and wire braid through a heated die to thereby embed the wire braid in the outer surface of the proximal inner tube.

In a preferred mode of operation, the steps of axially interconnecting the distal inner tube to the proximal inner tube having the reinforcing layer applied thereon and continuously covering the interconnected proximal and distal inner tubes with a sheath are continuously carried out by (a) alternately connecting proximal inner tubes and distal inner tubes to form a length of tubing, (b) continuously covering the entire length of tubing consisting of alternately connected proximal and distal inner tubes with a sheath, and (c) cutting the length at positions approximately intermediate of the proximal inner tubes and positions approximately intermediate of the distal inner tubes into catheters each comprising a pair of proximal and distal inner tube sections.

DESCRIPTION OF THE PREFERRED EMBODIMENTS

Figure 1:
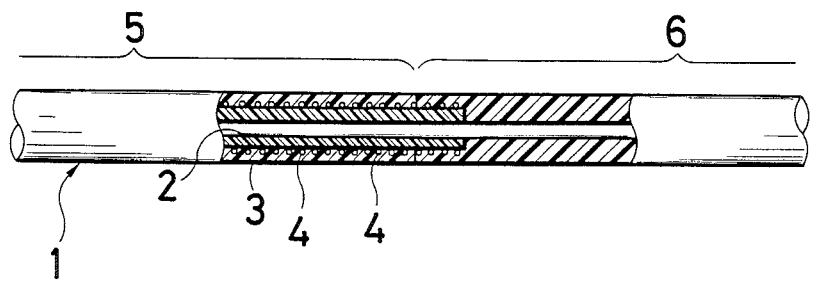
FIG. 1 is a partially cutaway view showing a joint part of a prior art catheter.

Referring to FIG. 1, there is shown a catheter disclosed in Stevens, U.S. Pat. No. 3,485,234 as a typical example of prior art catheters. The catheter designated at 1 comprises body and tip portions 5 and 6. A wire braid 4 is sandwiched between flexible inner and outer tubes 2 and 3 to form body portion 5 having a relatively low flexibility. Tip portion 6 which is relatively soft is connected to one end of body portion 5 from which part of outer tube 3 has been removed.

However, body portion 5 and tip portion 6 of catheter 1 can form steps along both the inner and outer surfaces at the joint. Such steps make it difficult to smoothly insert the catheter into a blood vessel and may result in damage to the vessel wall or even thrombus formation. A poor connection between body portion 5 and tip portion 6 can also result in the separation of the catheter into these two parts.

Figure 2:
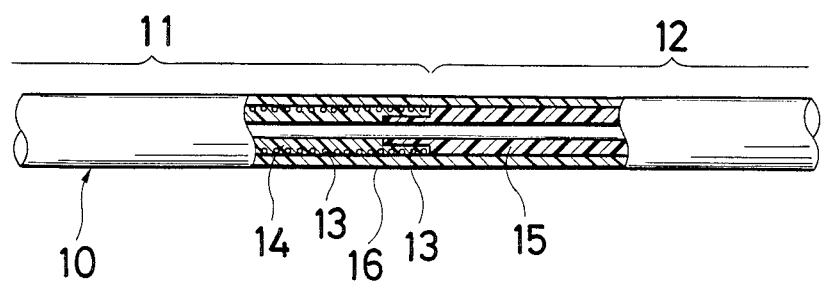
FIG. 2 is a partially cutaway view showing a joint part of a catheter according to a first embodiment of the present invention.

FIG. 2 is a partially cutaway view showing one part of a catheter according to a first embodiment of the present invention. The catheter designated at 10 is formed by the axial interconnection of a body portion 11 with a tip portion 12 having different physical properties from the body portion. More specifically, the catheter 10 is comprised of the body portion 11 including a proximal inner tube 14 and a reinforcing layer 13 in the form of a wire braid, a distal inner tube 15 connected to the body portion 11, and a sheath 16 continuously covering the entire length of interconnected body portion 11 and distal inner tube 15. The inside surface of proximal inner tube 14 and the inside surface of distal inner tube 15 are connected together in a substantially smooth and continuous fashion by enlarging the inside diameter of proximal inner tube 14 at the end to be joined while reducing the outside diameter of distal inner tube 15 at the end to be joined, and then fitting the reduced outside diameter end of the distal inner tube into the enlarged inside diameter end of the proximal inner tube followed by heat welding.

Proximal and distal inner tubes 14 and 15 are formed of materials having different physical properties. More specifically, distal inner tube 15 will at times be more flexible or more elastically deformable than proximal inner tube 14. There will also be cases in which distal inner tube 15 be of a plastically deformable material while proximal inner tube 14 be of an elastically deformable material. For example, a catheter having a less flexible body portion and a more flexible tip portion may be obtained by forming proximal inner tube 14 from a polyamide elastomer, and distal inner tube 15 from a plasticized polyamide elastomer, for example, with a plasticizer such as ethylhexyl p-hydroxy benzoate (POBO) or a polyolefin elastomer.

Other materials of which the proximal inner tube may be made include polyamide, polyurethane, polyvinyl chloride, polyethylene, and polypropylene resins. For the distal inner tube, a proper choice may be made from the above resins, depending on the intended application and the particular proximal inner tube material used. As is evident from the example of polyamide elastomers given above, different physical properties may be imparted to the body and tip portions of the same base resin through the use of amounts of plasticizer appropriate to the respective portions.

Flexibility is one of the physical properties that differ in the body and tip portions. Flexibility difference can typically be obtained from the plasticized and unplasticized polyamide elastomers just mentioned. As for plastic deformation of the tip portion, this can preferably be achieved by forming the proximal inner tube from a polyamide elastomer and the distal inner tube from polyethylene. Moreover, the material of which the catheter distal inner tube 15 is made may desirably contain a radiopaque substance such as barium sulfate or bismuth subcarbonate. A polyamide elastomer is a typical composition allowing larger amounts of radiopaque substance to be incorporated therein.

Sheath 16 of catheter 10 may be formed from the same material as proximal inner tube 14 or distal inner tube 15, or from a material having an elasticity intermediate to those of proximal and distal inner tubes 14 and 15. Preferably, to ensure formation of a smooth outer surface, the material of which sheath 16 is made does not contain any radiopaque substances. It is also desirable that proximal inner tube 14, distal inner tube 15, and sheath 16 be formed of materials compatible with each other. More preferably, all the materials are compounded from the same type of resin. If the inner tubes 14, 15 and sheath 16 are formed from less compatible materials, an adhesive layer compatible with both the inner tubes and the sheath may be provided therebetween.

The dimensions of catheter 10 may be typically as follows: inside diameter of proximal and distal inner tubes 14 and 15, 0.5–2.0 mm; outside diameter of sheath 16, 1–3 mm; wall thickness of sheath 16, 0.05–0.25 mm; total wall thickness, 0.25–0.5 mm.

It is also possible to ensure the response of tip portion 12 to rotation of body portion 11 by employing a stainless steel wire with a diameter of 0.03–0.10 mm in reinforcing layer 13. Reinforcing layer 13 may preferably be formed by braiding such a wire to provide even better response to rotation of the body portion.

It is also desirable that reinforcing layer 13 be fully embedded in proximal inner tube 14 to provide a smooth outer surface and that the outside diameters of reinforcing layer 13 and distal inner tube 15 be substantially equal. Then the wall thickness of sheath 16 may be substantially equal on both the proximal and distal sides of catheter 10 so that sheath 16 may be more readily molded. In addition, the outer surface of sheath 16 is not affected by surface irregularities in reinforcing layer 13, making it possible to provide the sheath with a smooth outer surface even at a reduced wall thickness. As compared with the case where a wire braid or reinforcing layer is on top of the surface of the proximal inner tube, the inside diameters of inner tubes 14 and 15 may also be enlarged without increasing the outside diameter of sheath 16.

A catheter hub is then connected to the end of body portion 11, and the necessary curved shape given to tip portion 12. At this point, catheter 10 is ready for use. Catheter 10 may be made anticoagulating by coating sheath 16 with an anticoagulant such as heparin and an antithrombic agent such as hydroxyethylmethacrylate-styrene copolymer. A suitable lubricant such as silicone oil may also be applied for low friction.

A catheter comprising a less flexible body portion and a more flexible tip portion integrally connected to the body portion is presented by the first embodiment of the present invention. Since the body portion is less flexible than the tip portion and a step is not formed between the surfaces of the two interconnected portions at the joint therebetween, the catheter can be smoothly inserted and advanced into the blood vessel or other body cavity without accompanying vascular wall damage or thrombus formation. There is no chance of body portion 11 and tip portion 12 separating.

A catheter comprising a body portion and a plastically deformable tip portion can be achieved through another choice of materials as described in connection with the first embodiment. Accordingly, the catheter can be inserted reliably and confidently as by bending or otherwise deforming the tip portion into a shape suited to insertion into any intended body cavity of complex shape, regardless of individual variations among different patients in the shape of the cavity, because of the less flexibility of the tip portion and the absence of a step at the joint between the body and tip portions. In this way, there is no risk of vascular wall damage, thrombus formation, or separation of the body and tip portions.

Figure 3:
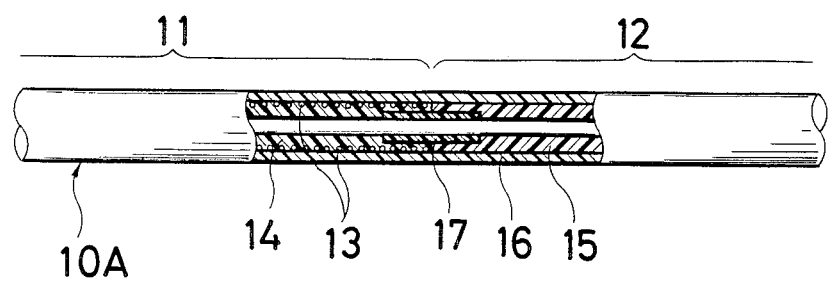
FIG. 3 is a partially cutaway view showing a joint part of a catheter according to a second embodiment of the present invention.

FIG. 3 is a partially cutaway view showing a joint portion of a catheter 10A according to a second embodiment of the present invention. Catheter 10A differs from catheter 10 of the first embodiment in that proximal inner tube 14 and distal inner tube 15 are connected via a joint tube 17 of a synthetic resin or metal having an inside diameter equal to that of the inner tubes. In other words, by enlarging the inside diameters of proximal and distal inner tubes 14 and 15 at the respective ends to be joined, and snuggly fitting joint tube 17 into the shouldered areas of enlarged inside diameter, the inner surfaces of proximal inner tube 14 and distal inner tube 15 can be connected in a smooth and continuous fashion.

It is also possible in this second embodiment to obtain a catheter 10A comprising a less flexible body portion 11 and a more flexible tip portion 12 integrally connected to the body portion without forming a step at the joint between them.

We will now describe the method for producing the catheter 10 described above while referring to FIGS. 4 through 12.

Figure 4:
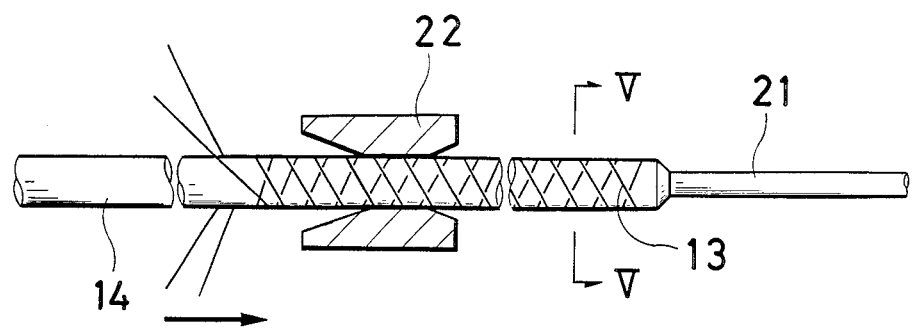
FIG. 4 illustrates the step of forming a reinforcing layer in a proximal inner tube.
Figure 5:
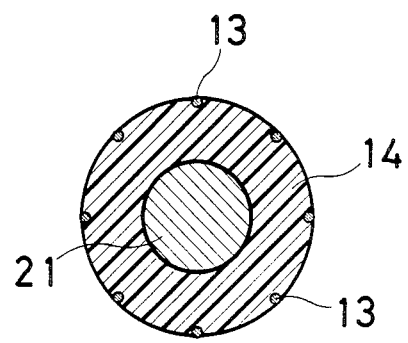
FIG. 5 is a radial cross-sectional view of the proximal inner tube having the reinforcing layer embedded therein.

First, a proximal inner tube 14 is molded by continuously coating a synthetic resin material such as a polyamide elastomer as mentioned earlier onto a ductile wire core 21, for example, silver or copper wire. Next, as shown in FIG. 4, a reinforcing layer 13 is formed by braiding reinforcing filaments or wires, for example, stainless steel wires about proximal inner tube 14. Proximal inner tube 14 with the reinforcing braid thereon is then passed through a heated die 22 having an opening of a relatively smaller diameter than the outside diameter of the braid to thereby embed the braid in the outer surface of proximal inner tube 14, forming the reinforcing layer-embedded proximal inner tube or reinforced proximal inner tube (FIG. 5). Alternatively, a reinforcement is braided at the same time as the proximal inner tube is molded. Such a simultaneously braided and molded tube is then passed through a heated die. At this point, the outside diameter of proximal inner tube 14 is equal to the opening diameter of heated die 22.

Next, proximal inner tube 14 having reinforcing layer 13 applied is cut, together with core 21, to a length slightly longer than twice the length of body portion 11 of catheter 10, and several centimeters of proximal inner tube 14 peeled away from both ends to leave core 21 exposed. Tension is then applied to the core at both ends to stretch the core to reduce its outside diameter, and the core withdrawn from proximal inner tube 14.

Figure 6:
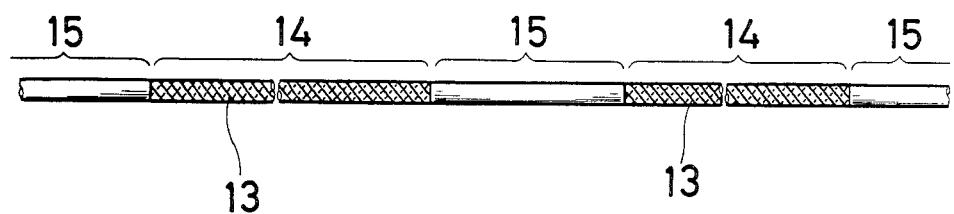
FIG. 6 is a side view showing a length of alternately connected distal and proximal inner tubes.
Figure 9:
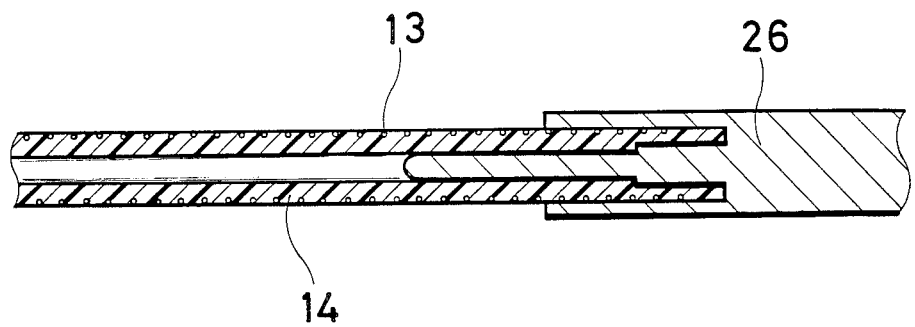
FIGS. 9 and 10 are cross-sectional views of the joint ends of the proximal and distal inner tubes placed in heated molds for reformation, respectively.
Figure 10:
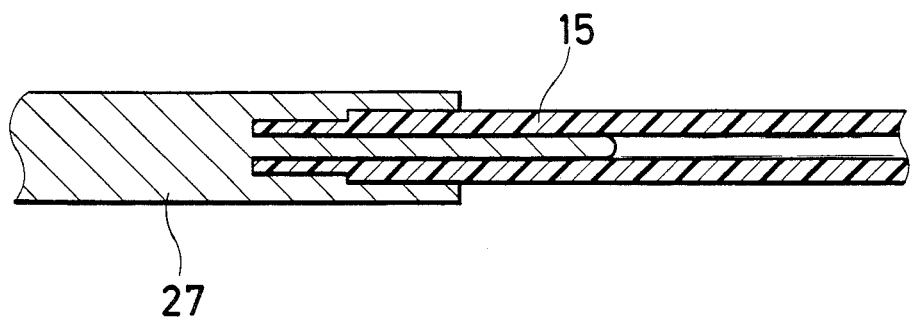
Figure 11:
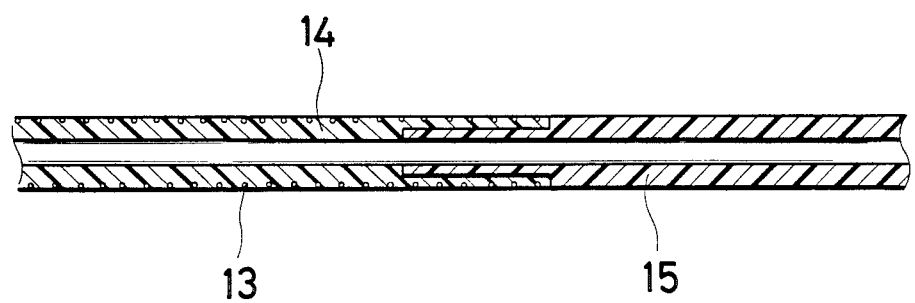
FIG. 11 is a cross-sectional view of the joint between proximal and distal inner tubes.

A distal inner tube 15 is separately extrusion molded. Distal inner tube 15 is equal in inside and outside diameters to reinforced proximal inner tube 14. The end portions of proximal and distal inner tubes 14 and 15 to be joined are reformed or tailored using heated molds 26 and 27 as shown in FIGS. 9 and 10. These tubes are then fitted and joined to each other by heat welding or any desired technique as shown in FIG. 11. By repeating the process, there is obtained as shown in FIG. 6 a length of alternately connected proximal and distal inner tubes 14 and 15.

Figure 7:
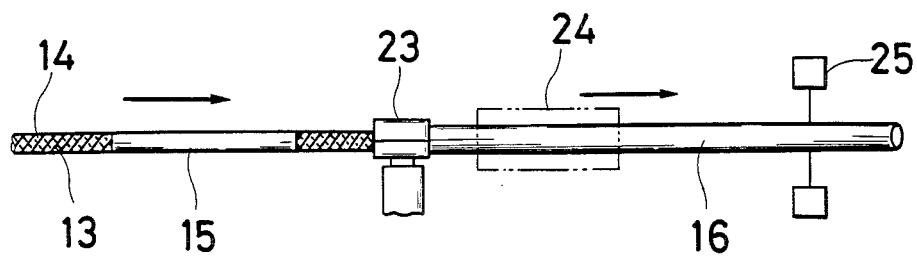
FIG. 7 illustrates the step of covering the entire length of interconnected proximal and distal inner tubes with a sheath.

Next, synthetic resin is continuously coated over the entire length of alternately connected proximal and distal inner tubes 14 and 15 by means of an extruder 23 as shown in FIG. 7, and then passed through a cooling trough 24 to form a sheath 16 as shown in FIG. 7. Next, proximal inner tubes 14 and distal inner tubes 15 are cut at the approximate centers thereof with a cutter 25, giving a catheter consisting of a body portion (proximal inner tube) and a tip portion (distal inner tube).

Figure 8:
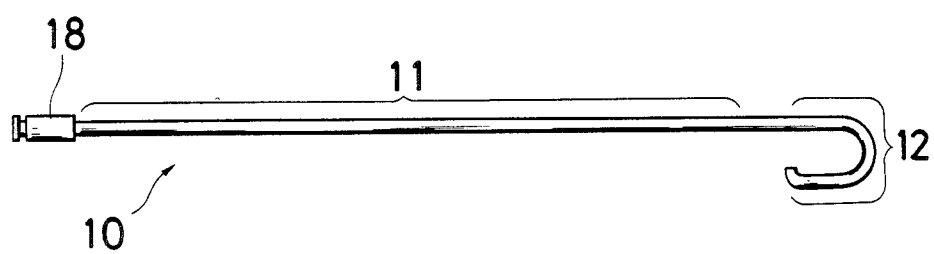
FIG. 8 is a side view showing the completed catheter.

Finally a series of finishing operations follow such as shaping of the chatheter tip, formation of side holes, and attachment of a hub 18, resulting in a catheter as shown in FIG. 8.

The method of producing a catheter just described permits the fabrication of a one-piece catheter wherein a relatively less flexible body portion 11 and a relatively more flexible tip portion 12 are integrally connected without forming a step at the junction therebetween. Moreover, the use of heated die 22 enables the reinforcing layer to be fully embedded within the outer surface of proximal inner tube 14.

By continuously covering the entire length of alternately interconnected proximal and distal inner tubes 14 and 15 with a sheath and cutting both the proximal and distal inner tubes at their approximate centers, sheaths 16 can be continuously formed for a plurality of catheters 10, raising the efficiency of catheter production.

The catheter of the present invention may also be produced by another method as will be described below.

Figure 12:
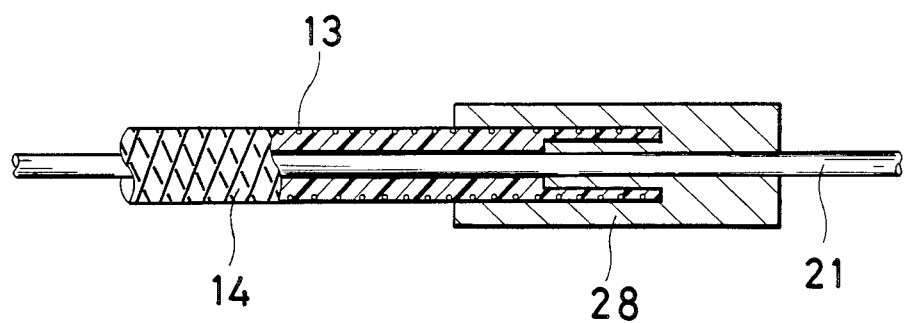
FIG. 12 is a cross-sectional view of the joint end of the proximal inner tube placed in a heated mold for reformation.

A proximal inner tube 14 having reinforcing layer 13 applied thereto as shown in FIG. 4 is cut to a length longer than the body portion 11 of catheter 10 with core 21 still inserted. After a section of the proximal inner tube equal in length to tip potion 12 is removed or peeled from core 21, that end of the proximal inner tube is inserted into a heated mold 28 as shown in FIG. 12 to reform the end configuration.

A distal inner tube 15 is separately extrusion molded and one end of the distal inner tube is reformed as shown in FIG. 10. The distal inner tube is then inserted over the exposed section of wire core 21, and proximal inner tube 14 and distal inner tube 15 joined such as by heat sealing.

Next, an assembly of proximal inner tube 14 and distal inner tube 15 interconnected over wire core 21 is passed through a tank of hot molten synthetic resin. A sheath 16 is formed while restricting the outside diameter of the resin covering the outer surface of inner tubes 14 and 15 with a die mounted on the tank outlet.

Next, the outside diameter of core 21 is reduced by applying tension to both ends of the core, and the core removed from inner tubes 14 and 15. The assembly of inner tubes 14 and 15 and sheath 16 is cut to the required length, giving catheter 10 comprised of body portion 11 and tip portion 12. Finally, a series of finishing operations follow such as shaping of the catheter tip, formation of side holes, and hub attachment.

As we have indicated above, the present invention provides a catheter comprising a body portion including a proximal inner tube and a reinforcing layer applied thereto, a tip portion including a distal inner tube axially interconnected to the body portion, the distal inner tube being made of a material having different physical properties from those of the proximal inner tube, a sheath continuously covering the body portion and the distal inner tube, wherein the outer surface of the body portion is substantially smooth and continuous to that of the distal inner tube. There is available a one-piece catheter comprising a relatively less flexible body portion and a relatively more flexible tip portion integrally connected thereto without forming a step at the joint.

In one embodiment of the catheter, the distal inner tube is made of a more flexible material than the proximal inner tube. The resultant catheter has a less flexible body portion and a more flexible tip portion.

In another embodiment of the catheter, the distal inner tube is made of a more plastically deformable material than the proximal inner tube.

In a further embodiment of the catheter, the reinforcing layer is braided in the body portion, achieving good response of the tip portion to rotation of the body portion.

In a further embodiment of the catheter, the outside diameters of the reinforcing layer and the distal inner tube are substantially equal. As a result, the wall thickness of the sheath is about the same on both the proximal and distal sides of the catheter, allowing the sheath to be molded in an easy and stable manner.

In a still further embodiment of the catheter, the reinforcing layer is fully embedded within the outer surface of the proximal inner tube. Then, the molding of the sheath is not affected by irregularities in the reinforcing layer, resulting in a smooth sheath surface at a reduced sheath wall thickness. The inside diameter of the inner tube may be enlarged with the same outside diameter of the sheath.

The present invention also provides a method for producing a catheter comprising the steps of molding a proximal inner tube, applying a reinforcing layer to the proximal inner tube, molding a distal inner tube from a material having different physical properties from those of the proximal inner tube, axially interconnecting the proximal inner tube to the distal inner tube while the outer surface of the proximal inner tube is substantially smooth and continuous to that of the distal inner tube, and continuously covering the interconnected proximal and distal inner tubes with a sheath. This method permits the easy fabrication of a catheter wherein a relatively less flexible body portion and a relatively more flexible tip portion are integrally joined without forming a step at the joint therebetween.

In a preferred embodiment, the reinforcing layer is applied to the proximal inner tube by winding reinforcing filaments or wires about the proximal inner tube and passing the proximal inner tube with the wire braid through a heated die to thereby embed the wire braid in the outer surface of the proximal inner tube. As a result, the reinforcing layer is fully embedded in the proximal inner tube adjacent its outer surface.

In addition, this invention provides a continuous catheter producing method. The steps of axially interconnecting the distal inner tube to the proximal inner tube having the reinforcing layer applied thereon continuously covering the interconnected proximal and distal inner tubes with a sheath can be carried out by (a) alternately connecting proximal inner tubes and distal inner tubes to form a length of tubing, (b) continuously covering the entire length of tubing consisting of alternately connected proximal and distal inner tubes with a sheath, and (c) cutting the length at positions approximately intermediate of the proximal inner tubes and positions approximately intermediate of the distal inner tubes into catheters each comprising a pair of proximal and distal inner tube sections. The continuous method enables the continuous formation of sheaths for a plurality of catheters, raising the efficiency of catheter production.

What is claimed is:

1. A catheter comprising
a body portion including a proximal inner tube made of an elastomer and a reinforcing layer embedded in the surface of the proximal inner tube; and
a tip portion including a distal inner tube made of a radiopaque substance-containing material and which is more flexible than said elastomeric proximal inner tube;
said reinforcing layer of said proximal inner tube comprising a metal material wire braiding to provide an increased response of said tip portion to rotation of said body portion;
said proximal inner tube having substantially the same outside diameter as said distal inner tube, said proximal inner tube being axially interconnected to said distal inner tube at a joint via radially and axially directed joint surfaces, the outer diameters of said proximal and distal inner tubes being substantially the same at least at portions thereof adjacent said radially and axially directed joint surfaces to provide a substantially smooth and continuous connection at least on the outer surfaces of said interconnected proximal and distal inner tubes; and
said body and said tip portions including a sheath of a radiopaque substance-free elastomer continuously covering the outer surface of said proximal inner tube and the outer surface of said distal inner tube and bonded to the outer surfaces of said proximal and distal inner tubes at least at the portions thereof in the vicinity of said joint surfaces.

2. The catheter of claim 1, wherein each of said proximal and distal inner tubes at said joint has a radial surface extending from an inner surface thereof, another radial surface extending from the outer surface thereof, and a circumferential surface axially extending between said radial surfaces, said proximal and distal inner tubes being fitted with each other at said joint.

3. The catheter of claim 1, wherein each of said proximal and distal inner tubes at said joint has a recess in its inner surface, and comprising a joint tube snugly fitted in said recesses.

4. The catheter of claim 1, wherein said proximal inner tube, said distal inner tube, and said sheath are made of polyamide elastomer base materials.

5. The catheter of claim 1, wherein said reinforcing layer is braided.

6. The catheter of claim 1, wherein said reinforcing layer comprises a network of braided stainless steel wire.

7. The catheter of claim 6, wherein said stainless steel wire has a diameter of 0.03 to 0.10 mm.

8. The catheter of claim 1, wherein said distal inner tube is made of a polyamide elastomer plasticized with ethylhexyl para-hydroxybenzoate.

9. The catheter of claim 1, wherein said proximal and distal inner tubes each have an inside diameter of 0.5 to 2.0 mm; said sheath has an outside diameter of 1 to 3 mm and a wall thickness of 0.05 to 0.25 mm; and said catheter has a total wall thickness of 0.15 to 0.5 mm.

10. The catheter of claim 1, wherein said sheath is coated with an anticoagulant.

11. The catheter of claim 1, wherein said sheath is bonded to said proximal and distal inner tubes over substantially the complete outer surfaces of said proximal and distal inner tubes.

12. The catheter of claim 1, wherein said proximal and distal inner tubes have substantially the same outer diameter over the complete length thereof.

13. The catheter of claim 12, wherein said sheath is bonded to said proximal and distal inner tubes over substantially the complete outer surfaces of said proximal and distal inner tubes.

14. The catheter of claim 1, wherein said distal inner tube is made of a material which is more flexible than said elastomeric material of said proximal inner tube.

15. The catheter of claim 1, wherein said sheath is extruded over said body portion and said distal inner tube.

16. A catheter comprising
a body portion including a proximal inner tube made of an elastomer and a reinforcing layer embedded in the surface of the proximal inner tube; and
a tip portion including a distal inner tube made of a plastically deformable material containing a radiopaque substance;
said reinforcing layer of said proximal inner tube comprising a metal material wire braiding to provide an increased response of said tip portion to rotation of said body portion;
said proximal inner tube having substantially the same outside diameter as said distal inner tube, said proximal inner tube being axially interconnected to said distal inner tube at a joint via radially and axially directed joint surfaces, the outer diameters of said proximal and distal inner tubes being substantially the same at least at portions thereof adjacent said radially and axially directed joint surfaces to provide a substantially smooth and continuous connection at least on the outer surfaces of said interconnected proximal and distal inner tubes;
said body and said tip portions including a sheath of a radiopaque substance-free elastomer continuously covering the outer surface of said proximal inner tube and the outer surface of said distal inner tube and bonded to the outer surfaces of said proximal and distal inner tubes at least at the portions thereof in the vicinity of said joint surfaces.

17. The catheter of claim 16, wherein each of said proximal and distal inner tubes at said joint has a radial surface extending from an inner surface thereof, another radial surface extending from the outer surface thereof, and a circumferential surface axially extedning between said radial surfaces, said proximal and distal inner tubes being snugly fitted with each other at said joint.

18. The catheter of claim 16, wherein each of said proximal and distal inner tubes at said joint has a recess in its inner surface, and comprising a joint tube snugly fitted in said recesses.

19. The catheter of claim 16, wherein said proximal inner tube and said sheath are made of a polyamide elastomer.

20. The catheter of claim 16, wherein said reinforcing layer is braided.

21. The catheter of claim 16, wherein said reinforcing layer comprises a network of braided stainless steel wire.

22. The catheter of claim 16, wherein said sheath is bonded to said body portion and said distal inner tube over substantially the complete outer surfaces of said proximal and distal inner tubes.

23. The catheter of claim 16, wherein said proximal and distal inner tubes have substantially the same diameter over the complete length thereof.

24. The catheter of claim 23, wherein said sheath is bonded to said body portion and said distal inner tube over substantially the complete outer surfaces of said proximal and distal inner tubes.

25. The catheter of claim 16, wherein said sheath is an extruded layer covering said outer surfaces of said proximal and distal inner tubes.

26. The catheter of claim 16, wherein said proximal and distal inner tubes each have an inside diameter of 0.5 to 2.0 mm; said sheath has an outside diameter of 1 to 3 mm and a wall thickness of 0.05 to 0.25 mm; and said catheter has a total wall thickness of 0.25 to 0.5 mm.

27. The catheter of claim 16, wherein said sheath is coated with an anticoagulant.

28. The catheter of claim 1, wherein said reinforcing layer of said body portion is arranged to assist in increasing the response of said tip portion to rotation of said body portion.

29. The catheter of claim 28, wherein said reinforcing layer is braided in said body portion.

30. The catheter of claim 16, wherein said reinforcing layer of said body portion is arranged to assist in increasing the response of said tip portion to rotation of said body portion.

31. The catheter of claim 30, wherein said reinforcing layer is braided in said body portion.

32. The catheter of claim 1, wherein said wire braiding is stainless steel wire braiding.

33. The catheter of claim 16, wherein said wire braiding is stainless steel wire braiding.

* * * * *

UNITED STATES PATENT AND TRADEMARK OFFICE
CERTIFICATE OF CORRECTION

PATENT NO. : 4,842,590
DATED : June 27, 1989
INVENTOR(S) : TANABE et al

It is certified that error appears in the above-identified patent and that said Letters Patent is hereby corrected as shown below:

Column 2, line 4, delete "to".

Column 9, line 26 (claim 9), "0.15 to 0.5 mm." should read -- 0.25 to 0.5 mm. --.

Column 10, line 14 (claim 17), "extedning" should read -- extending --.

Signed and Sealed this

Fourth Day of September, 1990

Attest:

HARRY F. MANBECK, JR.

Attesting Officer     Commissioner of Patents and Trademarks